(12) United States Patent
Graczyk

(10) Patent No.: US 6,349,726 B1
(45) Date of Patent: Feb. 26, 2002

(54) LASER SURGERY EYE SHIELD

(76) Inventor: Paul M. Graczyk, 61 Brookside Dr., Glendale Heights, IL (US) 60139

( * ) Notice: Subject to any disclaimer, the term of this patent is extended or adjusted under 35 U.S.C. 154(b) by 0 days.

(21) Appl. No.: 09/336,879

(22) Filed: Jun. 18, 1999

(51) Int. Cl.[7] .................................................. A61F 9/00
(52) U.S. Cl. ........................... 128/858; 128/853; 606/1; 606/5; 606/10
(58) Field of Search .............................. 606/1, 3–6, 10, 606/13; 128/853, 858

(56) References Cited

U.S. PATENT DOCUMENTS

| | | | |
|---|---|---|---|
| 3,074,407 A | 1/1963 | Moon | |
| 4,653,495 A | * 3/1987 | Nanaumi | 606/9 |
| 4,688,570 A | 8/1987 | Kramer | |
| 4,739,761 A | 4/1988 | Grandon | |
| 4,903,695 A | * 2/1990 | Warner et al. | 606/5 |
| 5,163,934 A | * 11/1992 | Munnerlyn | 606/5 |
| 5,312,428 A | 5/1994 | Lieberman | |
| 5,368,590 A | 11/1994 | Itoh | |
| 5,505,723 A | 4/1996 | Muller | |
| 5,616,139 A | 4/1997 | Okamoto | |
| 5,772,675 A | 6/1998 | Hellenkamp | |
| 5,807,380 A | 9/1998 | Discher | |
| 5,833,701 A | 11/1998 | Gordon | |

* cited by examiner

Primary Examiner—David M. Shay
(74) Attorney, Agent, or Firm—Robert L. Marsh

(57) ABSTRACT

A shield is provided to protect the outer portions of the cornea and the under surface of a cap of the cornea during LASIK surgery comprising an annular body with a concave lower surface and a central opening, The central opening is sized to be a little smaller than the outer diameter of the cut made to form the cap. The shield is positioned on the upper surface of the cornea and the folded cap to protect the outer edges thereof from exposure to the ray of the laser.

6 Claims, 1 Drawing Sheet

LASER SURGERY EYE SHIELD

The present invention relates to laser surgery for correcting myopia and hyperopia and in particular to a shield to protect the peripheral portions of the cornea from the laser during the course of such surgery.

BACKGROUND OF THE INVENTION

Laser surgery can be used to remove portions of the cornea of the eye thereby reshaping the cornea to correct myopia and hyperopia. During such surgery, a portion of the cornea is removed by the laser thereby reshaping the surface of the cornea to change the focal length of the lens to compensation for the effects of myopia and hyperopia.

To undertake such surgery, it is desirable to remove the upper surface of the cornea such that the lower portion of the cornea is exposed to the laser during surgery. After the laser has reshaped a lower portion of the cornea, the upper surface is replaced and eye is allowed to heal.

A preferred procedure known as Laser Assisted Interastromal Keratomileusis, commonly known as "LASIK", involves the cutting of a dome shaped cap from the cornea with a portion of the cap still attached to the cornea to form a hinge. The cap is then folded backwards to expose a lower portion of a cornea. The laser is then used to reshape the lower portion of the cornea, and after the lower portion has been reshaped the cap is repositioned and allowed to heal. The procedure is described in Dishler U.S. Pat. No. 5,807,380.

During LASIK surgery, the laser beam should be directed at only the lower portion of the cornea exposed after removal of the cap, and it is undesirable for the laser to strike the peripheral edge of the opening formed when the cap has been removed or the fold which constitutes the hinge allowing the cap to be folded backward. It would, therefore, be desirable to provide an improved method and apparatus for protecting the vulnerable portions of the cornea from damage by the laser during laser surgery.

SUMMARY OF THE INVENTION

Briefly, the present involves an apparatus and a method of performing laser eye surgery comprising the steps of cutting a cap a material from the outer surface of the cornea of the eye to form a flap having given outer dimensions and a joined edge forming a hinge. The cap is then folded backwards along the joined edge to expose the lower portion of the cornea which is to be re-contoured by the beam of a laser.

In accordance with the invention, an annular shield is provided having a central opening with dimensions which do not exceed the given dimensions of the perimeter of the cap and having a concave lower surface which is complimentary to the shape of the outer surface of an eye. Preferably, a plurality of such shields are provided, with each of such shields having a different sized central opening such that a shield having a central opening sized to best fit the size of the cap of the cornea can be selected for use with the eye undergoing surgery.

The annular shield is positioned with the lower surface thereof upon the eye and over the folded flap with the lower portion of the cornea exposed through the central opening. Thereafter, the laser beam is directed through the central opening to perform the surgery. In accordance with the present invention, the shield's lower surface is concave and complementary in shape to the outer surface of the eye and the central opening is sized to expose the lower layer of the cornea visible as the result of the removal of a portion which forms the cap. The cap is not entirely removed from the cornea, but is retained thereon by a small portion of the cornea, which serves as a hinge to allow the cap to be folded away and expose the lower portions thereof.

In the preferred embodiment, the central opening comprises approximately 270 degrees of a circle and the remaining 90 degrees is a cord connecting the distal ends of the partial circle. Since the shape of each patient's eye is different, a plurality of shields, each with a different sized central opening, are provided such that a shield having the central opening suitable for use during the surgery of a given eye is selected. Preferably, each shield is provided with a tab which can be grasped by a pair of tongs or any other suitable device for positioning the shield on the cornea of the eye with the cord of the central opening positioned along the crease of the fold to thereby protect the fold from the rays of the laser.

BRIEF DESCRIPTION OF THE DRAWINGS

A better understanding of the present invention will be had after a reading of the following detailed description taken in conjunction with the drawings wherein.

DETAILED DESCRIPTION OF THE PREFERRED EMBODIMENT

Figure 1:
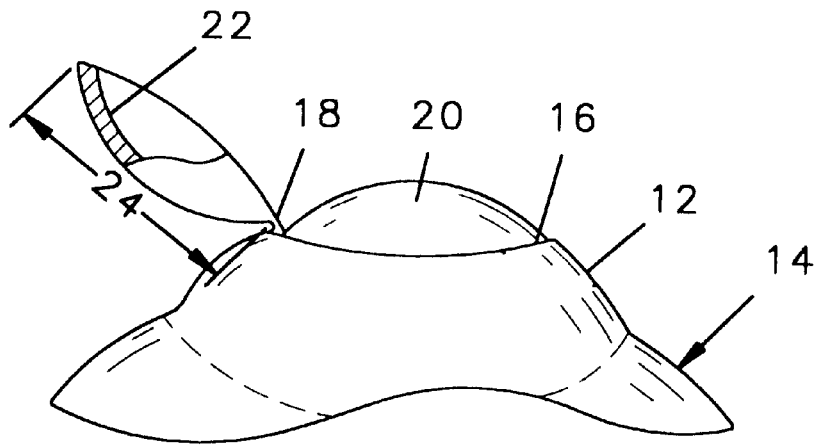
FIG. 1 is a fragmentary isometric view of an eye having a cap removed from the upper surface of the cornea to expose a lower portion thereof.
Figure 2:
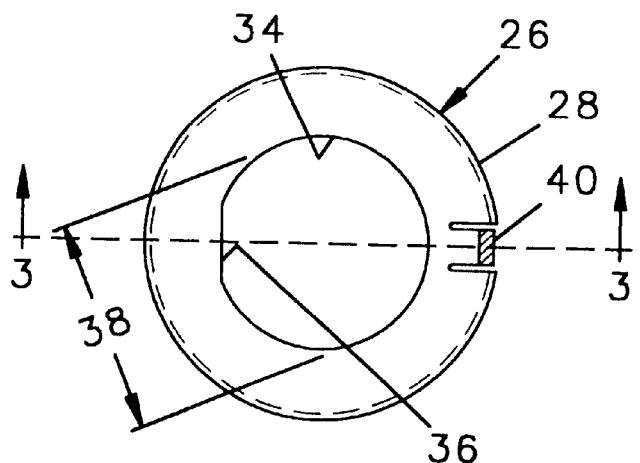
FIG. 2 is a front elevational view of a shield in accordance with the present invention fitted over an eye having a flap folded backwards and the lower portions of the cornea visible through the central opening of the shield.
Figure 3:
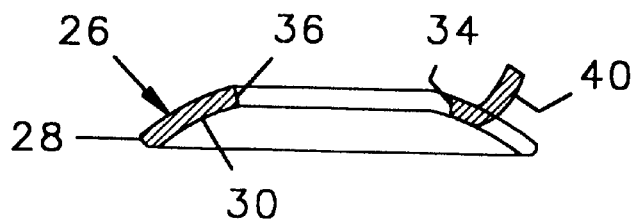
FIG. 3 is a cross sectional view of the shield shown in FIG. 2 taken through a line 3—3 thereof.

Referring to FIGS. 1–3, in accordance with the LASIK procedure, a dome shaped cap 10 is removed from the cornea 12 of an eye 14 by making a semi-circular peripheral cut 16 which does not close to a circle as shown. The uncut portion 18 serves as a hinge to permit the cap 10 to be folded away from the center of the cornea and leave exposed a lower layer 20 the cornea. In accordance with the LASIK procedure, the upper surface of the lower layer 20 is reshaped by subjecting the cornea to a precision operated laser, not shown.

It is desirable to apply the laser to the lower layer 20 without subjecting any of the upper surface of the cornea 12 which surrounds the cut 16, or the under surface 22 of the cap 10 thereto. A complicating factor is the problem of protecting the surrounding cornea and under surface of the cap is that there are minor differences between the shapes of the eyes of patients, and, as a result thereof, the outer diameter 24 to the cap 10 is different from one patient to another.

In accordance with the present invention, to protect the portion of the outer surface of the cornea 12 which surrounds the cut 16 and the under surface 22 of the cap 10, a shield 26 in accordance with the present invention is provided. The shield 26 is generally annular in shape, having a circular outer peripheral 28 and a concave lower surface 30 which is complimentary in shape to the outer surface of a human eye. The concave lower surface 30 defines a spherical surface having a radius of approximately one-half inch.

There are no fixed requirements for the outer diameter of a shield, but typically, the outer diameter 30 may be approximately 16.5 mm. The inner opening of the shield includes a semi circular portion 34 which defines approximately 270 degrees of a circle, and connecting the ends of the semi-circular portion is a cord 36 which defines the remaining 90 degrees of the central opening.

In accordance with the present invention, a plurality of shields 26 are provided, each one with a central opening having a different diameter 38 for the central opening thereof, such that a surgeon can select the desired shield 26 having an inner diameter 38 which is less than the diameter 24 of the cap 10 and of the cut 16. Accordingly, when the shield 26 is positioned over the center of the cornea 12, with the cord 36 positioned along the fold of the uncut portion 18, only the lower layer 20 can be seen through the central opening thereof. The edge of the cut 16, the portion of the cornea 12 surrounding the cut 16, and the under surface 22 of the cap 10 are all protected from the rays of the laser directed at the cornea of the eye by the shield 26.

In the preferred embodiment, the concave lower surface 30 of a shield 26 is polished so as not to cause irritation to the surface of the eye and the body of the shield 26 is made of any suitable material which can withstand and absorb the energy of the laser, not shown, without conducting excess heat to the surrounding eye.

The preferred embodiment will also include a protrusion 40 on the outer surface of the body of the shield 26 by which the shield 26 may be gripped with a tweezers or other suitable tool to enable the physician to position the shield 26 over the upper surface of the cornea 12 of an eye.

In the preferred embodiment, a plurality of shields 26 are provided in a set to thereby permit a surgeon to select the shield having an opening suitable for use on the eye of a patient who is to receive eye surgery using the LASIK procedure. Preferably, the inner diameter of a semi-circular portion 34 of the shields should range from a minimum of 0.50 mm to a maximum of 15.0 mm, with successive shields having a difference in diameter of approximately 0.50 mm.

While the present invention has been disclosed with respect to a single embodiment, it will be appreciated that many variations and modifications can be made without departing from the true spirit and scope of the present invention. Therefore, it is the intent of the following claims to cover all such modifications and variations which fall within the true spirit and scope of the invention.

What is claimed:

1. A shield for use in surgery on the cornea of an eye wherein a generally circular cap having a given diameter is cut from an upper portion of said cornea leaving an uncut portion to form a hinge for retaining said cap to said eye, said cap folded at said uncut portion away from a central portion of said cornea to expose a lower surface of said cornea, said lower surface bounded by an edge former by said cut, said shield comprising an annular body having a central opening and a lower surface, said central opening having an inner edge, said inner edge having a portion thereof defining a circle and a portion thereof defining a cord of said circle, said shield positionable on said eye with said portion defining a circle having a diameter less than said given diameter of said cap for protecting said outer edge of said lower surface of said cornea and said portion defining a cord sized for protecting said uncut portion retaining said cap to said eye.

2. A shield in accordance with claim 1 wherein said annular body has a concave lower surface.

3. A shield in accordance with claim 1 and further comprising means connected to said annular body for positioning said shield on said eye.

4. The method of performing eye surgery comprising the steps of cutting a layer of material from the outer surface of the cornea of an eye to form a cap having a given diameter and leaving a portion of said cap uncut from said eye to form a hinge joining said cap to said cornea, folding said cap along said hinge to expose a lower portion of said cornea where said lower portion has an outer edge defined by said cutting of a layer of material, providing an annular shield having a central opening, said central opening having an inner edge having a portion thereof defining a circle having a diameter less than said given diameter of said cap and a portion of said opening defining a cord of said circle, and positioning said annular shield on said eye with said portion defining a circle covering said outer edge of said lower portion of said cornea and with said portion defining a cord covering said portion of said cap that is uncut from said eye to form a hinge.

5. The method of claim 4 and comprising the further steps of providing a laser, and directing said laser through said central opening of said shield and on to said lower portion of said cornea.

6. The method of claim 5 and further comprising the step of selecting said shield from a plurality of shields, where each of said plurality of shields has a different diameter of said portion of said central opening defining a circle.

* * * * *